US00PP15617P3

(12) United States Plant Patent

Cosner et al.

(10) Patent No.: US PP15,617 P3

(45) Date of Patent: Mar. 1, 2005

(54) *IMPATIENS* PLANT NAMED 'TICOPUR'

(50) Latin Name: *Impatiens walleriana*
Varietal Denomination: TiCoPur

(76) Inventors: Harlan B. Cosner, 14389 E. Evans Creek Rd., Rogue River, OR (US) 97537; Susan Cosner, 14389 E. Evans Creek Rd., Rogue River, OR (US) 97537

( * ) Notice: Subject to any disclaimer, the term of this patent is extended or adjusted under 35 U.S.C. 154(b) by 0 days.

(21) Appl. No.: 10/402,002

(22) Filed: Mar. 27, 2003

(65) Prior Publication Data

US 2004/0194185 P1 Sep. 30, 2004

(51) Int. Cl.[7] ..... A01H 5/00

(52) U.S. Cl. ..... Plt./317

(58) Field of Search ..... Plt./317

(56) References Cited

U.S. PATENT DOCUMENTS

PP11,426 P 6/2000 Cosner et al. ..... Plt./317

*Primary Examiner*—Anne Marie Grunberg
(74) *Attorney, Agent, or Firm*—Bradley M. Ganz; Ganz Law, P.C.

(57) ABSTRACT

A new and distinct double-flowered '*Impatiens walleriana*' plant name 'TiCoPur', producing bright purple flowers; dark green foliage; compact growth habit; fully double flowers held above or beyond the foliage on strong peduncles and pedicels; and a compact mounded growth habit.

1 Drawing Sheet

Latin name of the genus and species and variety denomination: '*Impatiens walleriana*' plant and known by the cultivar name 'TiCoPur'.

BACKGROUND—FIELD OF INVENTION

The present invention relates to a new and distinct cultivar botanically known as '*Impatiens walleriana*' and by the cultivar name 'TiCoPur', which is shown in the photograph accompanying this specification.

The cultivar was developed and selected in a controlled breeding program in a controlled environment in Broadbent, Oreg. by the inventors, Harlan Cosner and Sue Cosner, as described herein. The plants may be used in landscaping, window, and hanging baskets and flower gardens. The plants are generally classed as an annual bedding plant.

BACKGROUND—DESCRIPTION OF THE PRIOR ART

'TiCoPur' is compared with '*Impatiens walleriana*' named 'Deep Purple,' subject of U.S. Plant Pat. No. 11,426.

COMPARISON

The *impatiens* plant of the present invention differs from prior plants, namely 'Deep Purple' in at least the following ways:

1. The flower color of 'TiCoPur' is lighter than that of 'Deep Purple'.
2. The plant of 'Deep Purple' is much larger than plant of 'TiCoPur'.
3. See accompanying comparison chart.

These and other distinguishing characteristics will be apparent to persons skilled in the art.

BACKGROUND—DISCOVERY AND PARENTAGE

The present cultivar was developed by standard cross-pollination. The pollen producing parent was an unpatented double-flowered '*Impatiens walleriana*' designated M-BR-9, and the seed producing parent was an unpatented semi-double-flowered *impatiens* designated P-BR-17A. The seed parent's flower color was purple, and the pollen parent's flower color was hot pink.

The cross was made in the breeders' controlled breeding program at Broadbent, Oreg. The first asexual reproduction was also made at Broadbent, Oreg. Successive asexual generations produced from cuttings with two or more leaves have shown the cultivar to be stable.

The cultivar is unique either in one or a combination of the characteristics described herein. It is a new double-flowered '*Impatiens walleriana*' producing bright purple flowers; dark green foliage; compact growth habit; fully double flowers held above or beyond the foliage on strong peduncles and pedicels; and a compact mounded growth habit.

Color references are according to The Royal Horticultural Society Colour Chart, except where general terms of ordinary dictionary significance are used.

DETAILED DESCRIPTION

The following description relates to the following environmental and cultural practices at Rogue River, Oreg., and was taken on or about Mar. 1, 2003.

The photograph illustrates the overall appearance of the cultivar described herein.

The photograph was taken of a 'TiCoPur' plant of about 10 weeks of age from rooted cuttings, at first inflorescence. There may be variations between the colors in the photograph and the colors in the following description due to light reflectance, or the amount of blue or red light captured in the film. If such variations occur, the written description shall control.

The plant of the present invention has not been observed in all possible environmental and/or cultural conditions. The phenotype may vary significantly with variations in environment such as temperature, light level, humidity and also with cultural practices such as fertility, soil, and water quality.

Container—6-inch Azalea containers.

Medium—Peat-lite type of soil less medium.

Greenhouse covering—Double layer Polyethylene with 50% shade applied above the covering.

Minimum temperature—70° F.

Maximum temperature—75° F.

Light levels—1000 to 1500 ft candles.

Fertilizer—20-10-20 with trace elements applied twice followed by one leaching with clear water.

Cutting type—Lateral stems with two or more leaves.

Propagation:

*Type of cutting.*—Lateral stems with two or more leaves were used for asexual reproduction.

*Time to initiate roots.*—Generally about 7 to 10 days at soil temperature of 72° F.

Appearance and form of mature plant:

*Plant form and habit.*—Mounded and of medium vigor.

*Plant size.*—Plants mature at about 16 cm. in height and about 30 cm. in width. Both of these measurements are a function of age, environmental and cultural practices, and can vary accordingly.

*Rooting description.*—The roots are fibrous and well-branched.

*Rooting ability.*—Easy, no hormones needed.

*Branching habit.*—Plants are self-branching. Stems are strong and freely produced. The number of stems depends upon cultural practices, age of stems used as cuttings and the number of growth buds present on the cutting when stuck.

*Stems.*—Stems are freely produced and no pinching to induce branching is needed. Color is between 146A and 146B with tiny dark markings of a very hard to determine color that appears to be close to 183B. The stems at maturity are generally at least 3 mm in diameter at the internodes, and the internode length is generally at least 0.5 cm in length.

*Foliage shape and size.*—Shape is ovate with cuneate to attenuate base; crenate margin, margin having tiny spines of an undeterminable reddish to brownish red color and each being less than 0.1 mm in length and protruding outwards in a perpendicular direction from leaf edge and parallel to the flat surfaces of the leaf margin between the lobes of the crenate margin; and an acuminate apex. Size of largest is about 5 cm long; about 4 cm wide.

*Foliage color.*—Adaxial surface close to 147A; abaxial surface close to 147C; abaxial surface venation is close to 146A; Adaxial surface venation, main vein at base is closest to 146A, lateral veins are barely distinguishable but appear closest to 146A.

*Foliage texture.*—Smooth and flat.

*Petioles.*—Longest petioles are about 3.5 cm long, half round, flat to slightly convex on upper surface which is about 4 mm wide, depth (from the upper surface to the bottom surface) of about 2.5 mm. Adaxial surface color appears to be 146B; abaxial surface color appears to be close to 146C.

*Natural flowering season.*—Year around in greenhouse conditions, and the frost-free period from spring through fall when planted outdoors. Flowers are produced continuously throughout the flowering season.

*Bud size, shape & color.*—The buds prior to opening are about 1 cm. in length; about 0.75 cm. in diameter; shape is ovate. Bud color prior to opening is close to 145A on top and close to 149D on bottom.

*Time to flower.*—Flowering begins at about 10 weeks form rooted cuttings.

*Duration of flower.*—Each flower generally lasts about 5 days at 75° F. maximum and 70° F. minimum temperature.

*Flowers borne.*—Above or beyond the foliage.

*Flower count.*—Usually two or more open flowers per stem and generally 15 or more from visible buds to fully mature flowers.

*Flower texture.*—Smooth and satiny.

*Flower fragrance.*—None detected.

*Flower color.*—Petals/petaloids — Adaxial surface is close to 74A with a basal spot close to 67A. Abaxial surface is close to 74D with a basal spot close to 67A.

*Flower size and shape.*—Generally, at least 3.5 cm wide; generally at least 1 cm deep. The above measurements refer to the larger flowers, and the flower size was taken during winter low light when the flowers are the smallest. During spring and summer, the flowers are generally much larger than the above measurements and as much as double the described size.

*Petal size and shape.*—Generally, at least 3.5 cm wide; generally at least 1 cm deep. The largest petals are generally at least 1.5 cm. wide and at least 1.5 cm. deep; obovate to exaggerated obovate in shape with obtuse to retuse apex, entire margin, and cuneate to obtuse base. The above measurements refer to the average flowers; and the flower size was taken during winter low light when the flowers are the smallest, during spring and summer, the flowers are generally much larger than the above measurements.

*Petal/petaloid count.*—25 or more.

*Calyx.*—Calyx consists of generally one sepal and one spur. The spur is generally at least 2 cm long, and about 2 mm in diameter at sepal end; shape is an acicular tapering tube about 1 mm in diameter at the apex, and it is attached toward the base of the sepal in a peltate manner. Color is close to 145A at apex, 67A at base, and a purple tinged green not matching or close to any color in the chart. The sepal generally measures about 1 cm wide, and about 1.25 cm long; ovate in shape with an acute apex, entire margin, and obtuse to cordate base; adaxial surface is close to 149 D with a spot around where the spur connects close to 67A; the abaxial surface is close to 145D with a spot where the spur attaches close to 67A.

*Peduncles.*—Generally about 2.5 cm long; about 2 mm in diameter; colored close to 144A. Good strength.

*Pedicels.*—Generally two or more per peduncle. Each is generally at least 2.25 cm in length, and at least 1.5 mm in diameter. Color is close to 144A. Good strength.

*Reproductive organs.*—The reproductive organs are replaced with sterile petaloids.

*Disease resistance.*—Disease resistance has not been tested.

*Dampness resistance.*—The plant has shown a good ability to hold the flowers in an outward manner during summer rains.

*Cold/heat resistance.*—Plant flowers well in summer heat.

COMPARISON CHART TO PRIOR ART

| | 'TiCoPur' | 'Deep Purple' |
|---|---|---|
| Stems - color | Color is between 146A and 146B with tiny markings close to 183B | Close to 146B with 187B markings |
| Foliage - Size Abaxial color | about 5 cm long; about 4 cm wide close to 147C | About 5 cm long; about 3.5 cm wide 147B with reddish blotches close to 183D |
| Foliage - Abaxial venation color | close to 146A | Close to 148A |
| Foliage - Adaxial color | close to 147A | 147A |
| Foliage - Adaxial venation color | main vein at base is closest to 146A, lateral veins appear closest to 146A | 148A |
| Petiole - Size Adaxial color | about 3.5 cm long, 4 mm wide, depth of about 2.5 mm. appears to be 146B; | About 4.25 cm long and About 3 mm diameter Close to 148A with 187B markings at node end |
| Petiole Abaxial color | appears close to 146C | Same as adaxial color |
| Largest Petal/ Petaloid - Size Abaxial color | generally at least 1.5 cm. wide and at least 1.5 cm. deep close to 74D with a basal spot close to 67A | About 2.25 cm in length, about 2.5 cm in width 71D, some have markings lighter than 69D and lighter than 157D |
| Petal/ Petaloid Adaxial color | Close to 74A with a basal spot close to 67A. | Between 74A and 74B |
| Peduncle - Size color | about 2.5 cm long; about 2 mm in diameter; close to 144A. | About 3.5 cm long, about 2 mm in diameter 146B to 146C with reddish stripes |
| Pedicel - Size color | generally at least 2.25 cm in length, and at least 1.5 mm in diameter. close to 144A. | About 2.5 cm in length, between 1 and 2 mm. 146B to 146C with tiny reddish spots |

-continued

COMPARISON CHART TO PRIOR ART

| | 'TiCoPur' | 'Deep Purple' |
|---|---|---|
| Sepal - Size Adaxial color | generally measures about 1 cm wide, and about 1.25 cm long close to 149D with a spot around where the spur connects close to 67A; | About 1 cm wide and about 1 cm wide. Close to 149D with a spot close to 74C to 74D |
| Sepal Abaxial color | close to 145D with a spot where the spur attaches close to 67A | Close to 149D with a spot of 73B |
| Spur - Size color | generally at least 2 cm long, and about 2 mm in diameter at sepal end; and about 1 mm at apex close to 145A at apex, 67A at base, and a purple tinged green not matching or close to any color in the chart | About 3 cm Close to 146D with tinges of red close to 178B at apex |
| Buds - Size Color | about 1 cm. in length; about .75 cm. in diameter close to 145A on top and close to 149D on bottom. | About 1 cm long, about 0.7 cm diameter 145B to 145C |

COLOR CODE CHART

| | |
|---|---|
| Stems: | 146A, 146B, 183B |
| Foliage Abaxial surface: | 147C |
| Foliage Abaxial surface venation: | 146A |
| Foliage Adaxial surface: | 147A |
| Foliage Adaxial surface venation: | 146A |
| Petiole Abaxial surface: | 146C |
| Petiole Adaxial surface: | 146B |
| Petals/Petaloids Abaxial surface: | 74A, 67A |
| Petals/Petaloids Adaxial surface: | 74A, 67A |
| Buds: | 145A, 149D |
| Peduncles: | 144A |
| Pedicels: | 144A |
| Sepals adaxial surface: | 149D, 67A |
| Sepals abaxial surface: | 145D, 67A |
| Spur: | 145A, 67A |

What is claimed:

1. A new and distinct cultivar of double-flowered '*Impatiens walleriana*' plant named 'TiCoPur', as illustrated and described herein.

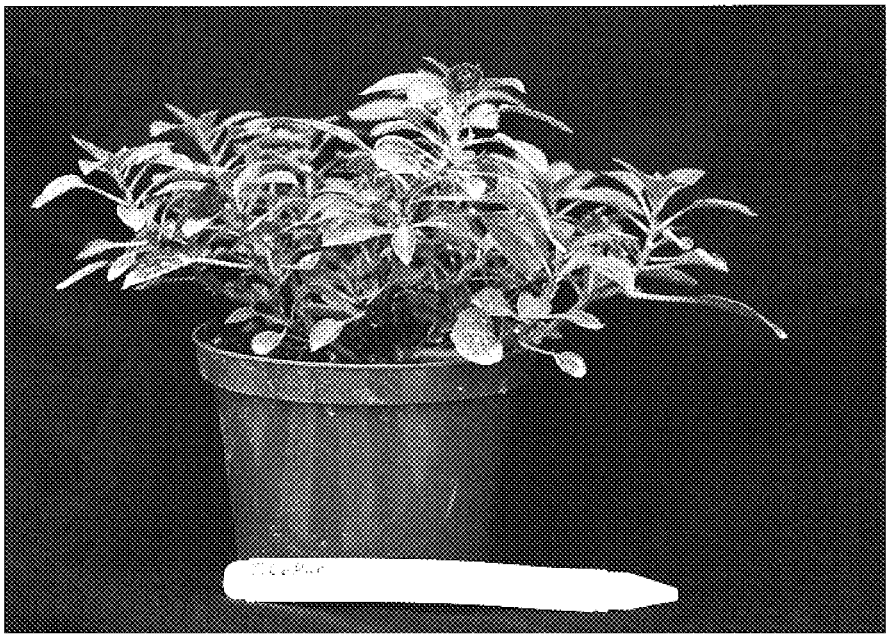

* * * * *